(12) United States Patent
Khanzhin

(10) Patent No.: US 12,065,462 B2
(45) Date of Patent: Aug. 20, 2024

(54) PURIFICATION OF OLIGOSACCHARIDES

(71) Applicant: GLYCOM A/S, Hørsholm (DK)

(72) Inventor: Nikolay Khanzhin, Humlebæk (DK)

(73) Assignee: Glycom A/S, Hørsholm (DK)

( * ) Notice: Subject to any disclaimer, the term of this patent is extended or adjusted under 35 U.S.C. 154(b) by 1046 days.

(21) Appl. No.: 16/626,217

(22) PCT Filed: Jun. 27, 2018

(86) PCT No.: PCT/IB2018/054750
§ 371 (c)(1),
(2) Date: Dec. 23, 2019

(87) PCT Pub. No.: WO2019/003135
PCT Pub. Date: Jan. 3, 2019

(65) Prior Publication Data
US 2020/0123184 A1    Apr. 23, 2020

(30) Foreign Application Priority Data

Jun. 30, 2017  (DK) .......................... PA 2017 70522
Jun. 30, 2017  (DK) .......................... PA 2017 70523
Jun. 30, 2017  (DK) .......................... PA 2017 70524

(51) Int. Cl.
| | | |
|---|---|---|
| C07H 1/06 | (2006.01) | |
| A23L 33/00 | (2016.01) | |
| B01D 61/02 | (2006.01) | |
| B01D 61/04 | (2006.01) | |
| B01D 61/14 | (2006.01) | |
| B01D 61/58 | (2006.01) | |
| B01D 69/02 | (2006.01) | |
| B01D 69/12 | (2006.01) | |
| B01D 71/56 | (2006.01) | |
| B01D 71/58 | (2006.01) | |
| C07H 3/06 | (2006.01) | |
| C08B 37/00 | (2006.01) | |
| C12P 19/04 | (2006.01) | |
| C12P 19/12 | (2006.01) | |
| C12P 19/18 | (2006.01) | |

(52) U.S. Cl.
CPC ............... *C07H 1/06* (2013.01); *A23L 33/40* (2016.08); *B01D 61/027* (2013.01); *B01D 61/04* (2013.01); *B01D 61/146* (2022.08); *B01D 61/58* (2013.01); *B01D 69/02* (2013.01); *B01D 69/12* (2013.01); *B01D 71/56* (2013.01); *B01D 71/58* (2013.01); *C07H 3/06* (2013.01); *C08B 37/0003* (2013.01); *C12P 19/04* (2013.01); *C12P 19/12* (2013.01); *C12P 19/18* (2013.01); *A23L 33/00* (2016.08); *A23V 2002/00* (2013.01); *B01D 61/145* (2013.01); *B01D 2315/16* (2013.01); *B01D 2325/20* (2013.01)

(58) Field of Classification Search
CPC .. C07H 1/06; C07H 3/06; A23L 33/40; A23L 33/00; B01D 61/027; B01D 61/04; B01D 61/146; B01D 61/58; B01D 69/02; B01D 69/12; B01D 69/125; B01D 71/56; B01D 71/58; B01D 61/145; B01D 2315/16; B01D 2325/20; C08B 37/0003; C12P 19/04; C12P 19/12; C12P 19/18; A23V 2002/00
See application file for complete search history.

(56) References Cited

U.S. PATENT DOCUMENTS

| | | |
|---|---|---|
| 5,827,714 A | 10/1998 | Yamamoto et al. |
| 6,255,094 B1 | 7/2001 | Yamamoto et al. |
| 7,521,212 B1 | 4/2009 | Samain et al. |
| 7,993,875 B2 | 8/2011 | Tsukamoto et al. |
| 8,187,853 B2 | 5/2012 | Yamamoto et al. |
| 8,372,617 B2 | 2/2013 | Yamamoto et al. |
| 2002/0148791 A1* | 10/2002 | DeFrees ................. C13K 13/00 536/53 |
| 2007/0020736 A1 | 1/2007 | Samain |
| 2007/0104843 A1* | 5/2007 | Holst ..................... A23C 9/142 426/491 |
| 2012/0121788 A1 | 5/2012 | Scott et al. |
| 2012/0184015 A1 | 7/2012 | Mine et al. |
| 2014/0170293 A1 | 6/2014 | Holst et al. |
| 2017/0204443 A1 | 7/2017 | Baumgïtner et al. |

FOREIGN PATENT DOCUMENTS

| | | | |
|---|---|---|---|
| EP | 0557580 A1 | 9/1993 | |
| EP | 1405856 A1 | 4/2004 | |
| EP | 2484686 A1 | 8/2012 | |
| EP | 2526784 A1 | 11/2012 | |
| EP | 2722394 A1 | 4/2014 | |
| WO | 9632492 | 10/1996 | |
| WO | 9815581 | 4/1998 | |
| WO | WO-9815581 A1 * | 4/1998 | ........... B01D 61/022 |
| WO | 9931224 | 6/1999 | |

(Continued)

OTHER PUBLICATIONS

Sterlitech, Crossflow Filtration Handbook (Jul. 25, 2017), pp. 12 (accessed Sep. 23, 2022). (Year: 2017).*
Google.com search for "Trisep UA60"; excited Sep. 23, 2022; (Year: 2022).*
Mao, et.al; Effect of NaCl addition during diafiltration on the solubility, hydrophobicity, and disulfide bonds of 80% milk protein concentrate powder; J. Dairy Sci. 95 :3481-3488 (Year: 2012).*
Crossflow Filtration Handbook; Thomasnet; Available Jul. 25, 2017; cover page and last two pages and internet page, 4 pages total . (Year: 2017).*
Sterlitech Archived Web Site: http://web.archive.org/web/20170503064129/https:/www.sterlitech.com/ge-osmonics-flat-sheet-membrane-gh-tfc-uf-cf016-5-pk.html; May 3, 2017; 4 pages. (Year: 2017).*

(Continued)

*Primary Examiner* — Clare M Perrin

(74) *Attorney, Agent, or Firm* — Neal, Gerber & Eisenberg LLP

(57) ABSTRACT

The invention relates to a method for separating sialylated oligosaccharides, preferably sialylated human milk oligosaccharides (HMOs), from disaccharides, preferably lactose, produced by a fermentation or enzymatic process.

20 Claims, No Drawings

(56) References Cited

FOREIGN PATENT DOCUMENTS

| WO | 0104341 A1 | 1/2001 |
|---|---|---|
| WO | 2005067962 A2 | 7/2005 |
| WO | 2006034225 A2 | 3/2006 |
| WO | 2007051475 A1 | 5/2007 |
| WO | 2007101862 A1 | 9/2007 |
| WO | 2010070104 A | 6/2010 |
| WO | 2010116317 A1 | 10/2010 |
| WO | 2010142305 A1 | 12/2010 |
| WO | 2012010889 A1 | 1/2012 |
| WO | 2012112777 A2 | 8/2012 |
| WO | 2012156897 A1 | 11/2012 |
| WO | 2012156898 A1 | 11/2012 |
| WO | 2012158517 A | 11/2012 |
| WO | 2013083623 A1 | 6/2013 |
| WO | 2013185780 A1 | 12/2013 |
| WO | 2014153253 A1 | 9/2014 |
| WO | 2015036138 A1 | 3/2015 |
| WO | 2015106943 A1 | 7/2015 |
| WO | 2015150328 A1 | 10/2015 |
| WO | 2016008602 A1 | 1/2016 |
| WO | 2016063262 A1 | 4/2016 |
| WO | 2016095924 A1 | 6/2016 |
| WO | 2016157108 A1 | 10/2016 |
| WO | 2016199069 A1 | 12/2016 |
| WO | 2016199071 A1 | 12/2016 |
| WO | 2017086443 A1 | 5/2017 |

OTHER PUBLICATIONS

Way Back Machine Document providing verification of the publication date of May 3, 2017 for Sterlitech archived citation; 1 page. (Year: 2017).*

Yushkin, A., et al., "Improvement of MWCO determination by using branched PEGs and MALDI method," Separation and Purification Technology, 2019, vol. 211, pp. 108-116.

Antoine, T. et al., "Highly Efficient Biosynthesis of the Oligosaccharide Moiety of the GD3 Ganglioside by Using Metabolically Engineered *Escherichia coli*," Angew. Chem. Int. Ed., 2005, vol. 44, pp. 1350-1352.

Aydogan, N. et al., "Effect of Operating Parameters on the Separation of Sugars by Nanofiltration," Separation Science and Technology, 1998, vol. 33(12), pp. 1767-1785.

Baumgärtner, F. et al., "Construction of *Escherichia coli* strains with chromosomally integrated expression cassettes for the synthesis of 20-fucosyllactose," Microbial Cell Factories, 2013, 13 pages. http://www.microbialcellfactories.com/content/12/1/40.

Cantarel, B.L. et al., "The Carbohydrate-Active EnZymes database (CAZy): an expert resource for Glycogenomics," Nucleic Acids Research, 2009, vol. 37, pp. D233-D238.

Chen, X. (2015)."Human Milk Oligosaccharides (HMOS): Structure, Function, and Enzyme-Catalyzed Synthesis," Elsevier Inc. (vol. 72), Advances in Carbohydrate Chemistry and Biochemistry, pp. 113-190. http://dx.doi.org/10.1016/bs.accb.2015.08.002.

Cobucci-Ponzano, B. et al., "b-Glycosyl Azides as Substrates for a-Glycosynthases: Preparation of Efficient a-L-Fucosynthases," Chemistry & Biology, 2009, vol. 16, pp. 1097-1108.

Córdova, A. et al., "Purification of galacto-oligosaccharides (GOS) by three-stage serial nanofiltration units under critical transmembrane pressure conditions," Chemical Engineering Research and Design, 43 pages, http://dx.doi.org/10.1016/j.cherd.2016.11.006.

Drouillard, S. et al. "Efficient synthesis of 60-sialyllactose, 6,60-disialyllactose, and 60-KDO-lactose by metabolically engineered *E. coli* expressing a multifunctional sialyltransferase from the *Photobacterium* sp. JT-ISH-224," Carbohydrate Research, 2010, vol. 345, pp. 1394-1399.

Drouillard, S. et al., "Large-Scale Synthesis of H-Antigen Oligosaccharides by Expressing Helicobacter pylori a1,2-Fucosyltransferase in Metabolically Engineered *Escherichia coli* Cells," Angew. Chem. Int. Ed. 2006, vol. 45, pp. 1778-1780.

Fierfort, N. et al., "Genetic engineering of *Escherichia coli* for the economical production of sialylated oligosaccharides," Journal of Biotechnology, 2008, vol. 134, pp. 261-265.

Gilbert, M. et al., The synthesis of sialylated oligosaccharides using CMP-Neu5Ac synthetase/sialyltransferase fusion, Nature Biotechnology, 1998, vol. 16, 99 769-772.

Goulas, A.K. et al., "Fractionation of oligosaccharides by nanofiltration," Journal of the Science of Food and Agriculture, 2003, vol. 83, pp. 675-680.

Goulas, A.K. et al., "Purification of oligosaccharides by nanofiltration," Journal of Membrane Science, 2002, vol. 209, pp. 321-335.

Han, N.S. et al., "Biotechnological production of human milk oligosaccharides," Biotechnology Advances, 2012, vol. 30, pp. 1268-1278.

Lee, W. et al., "Whole cell biosynthesis of a functional oligosaccharide, 2'-fucosyllactose, using engineered *Escherichia coli*," Microbial Cell Factories, 2012, 22 pages. https://doi.org/10.1186/1475-2859-11-48.

Lenntech. (2013) "Biotech Elements; Small Size Spiral-wound Elements for Lab Testing", 2 pages.

Li, W. et al., "Study on nanofiltration for purifying fructo-oligosaccharides: I. Operation modes," Journal of Membrane Science, 2004, vol. 245, pp. 123-129.

Luo, J et al., "An integrated membrane system for the biocatalytic production of 30-sialyllactose from dairy by-products," Bioresource Technology, 2014, vol. 166, pp. 9-16.

Martinez-Ferez, A. et al., "Goats' milk as a natural source of lactose-derived oligosaccharides: Isolation by membrane technology," International Dairy Journal, 2006, vol. 16, pp. 173-181.

Maru, I. et al., "Synthesis of Sialyllactose from N-Acetylneuraminic Acid and Lactose by a Neuraminidase from Arthrobacter ureafaciens," Biosci. Biotech. Biochem., 1992, vol. 56(10), pp. 1557-1561.

Masuda, M., et al., "Continuous Production of Sialyllactose from Colominic Acid Using a Membrane Reactor," Journal of Bioscience and Bioengineering, 2000, vol. 89(2), pp. 119-125.

Peirtsegaele, E. (2017) "Nanofiltration: The Newest Class of Membrane Filtration," Microdyn-Nadir US, Inc. 3 pages.

Mine, T. et al., "An α2,3-Sialyltransferase from *Photobacterium* sp. JT-ISH-224 Transfers N-Acetylneuraminic Acid to Both the O-2 and O-3' Hydroxyl Groups of Lactose," Journal of Carbohydrate Chemistry, 2010, vol. 29, pp. 51-60.

Mine, T. et al., "An α2,6-sialyltransferase cloned from Photobacterium leiognathi strain JT-SHIZ-119 shows both sialyltransferase and neuraminidase activity," Glycobiology, 2010, vol. 20(2), pp. 158-165.

Murata, T. et al., "Facile enzymatic conversion of lactose into lacto-N-tetraose and lacto-N-neotetraose," Glycoconjugate Journal, 1999, vol. 16, pp. 189-195.

Ninonuevo, M.R. et al., "A Strategy for Annotating the Human Milk Glycome," J. Agric. Food Chem., 2006, vol. 54, pp. 7471-7480.

Nordvang, R. T., et al. (2015). Production of prebiotic oligosaccharides by novel enzymatic catalysis. Technical University of Denmark, Department of Chemical and Biochemical Engineering. 142 pages.

Nordvang, R.T. et al., "Separation of 3'-sialyllactose and lactose by nanofiltration: A trade-off between charge repulsion and pore swelling induced by high pH," Separation and Purification Technology, 2014, vol. 138, pp. 77-83.

Osanjo, G. et al., "Directed Evolution of the R-L-Fucosidase from Thermotoga maritima into an R-L-Transfucosidase," Biochemistry, 2007, vol. 46, pp. 1022-1033.

Priem, B. et al., "A new fermentation process allows large-scale production of human milk oligosaccharides by metabolically engineered bacteria," Glycobiology, 2002, vol. 12(4), pp. 235-240.

Sano, M. et al., "An enzyme releasing lacto-N-biose from oligosaccharides," Proc. Natl. Acan. Sci. USA, 1992, vol. 89, pp. 8512-8516.

Sano, M. et al., "Purification and Characterization of an Enzyme Releasing Lacto-N-biose from Oligosaccharides with Type 1 Chain," The Journal of Biological Chemistry, 1993, vol. 268(25), pp. 18560-18566.

Sarney, D.B. et al., "A Novel Approach to the Recovery of Biologically Active Oligosaccharides from Milk Using a Combination

(56) References Cited

OTHER PUBLICATIONS of Enzymatic Treatment and Nanofiltration," Biotechnology and Bioengineering, 2000, vol. 69 (4), pp. 461-467.

Shoda, S. et al., "Chemo-enzymatic synthesis of novel oligo-N-acetyllactosamine derivatives having a b(1-4)-b(1-6) repeating unit by using transition state analogue substrate," Cellulose, 2006, vol. 13, pp. 477-484.

Ten Bruggencate, S.J.M. et al, "Functional role and mechanisms of sialyllactose and other sialylated milk oligosaccharides," Nutrition Reviews, 2014, vol. 72(6), pp. 377-389.

Urashima, T. et al. (2011) Nutrition and Diet Research Progress: Milk Oligosaccharides. New York: Nova Science Publishers, Inc. 92 pages.

Wada, J. et al., "1,2-alpha-L-Fucosynthase: A glycosynthase derived from an inverting alpha-glycosidase with an unusual reaction mechanism," FEBS Letters, 2008, vol. 582, pp. 3739-3743.

Wada, J. et al., "Bifidobacterium bifidum Lacto-N-Biosidase, a Critical Enzyme for the Degradation of Human Milk Oligosaccharides with a Type 1 Structure," Applied and Environmental Microbiology, 2008, vol. 74(13), pp. 3996-4004.

Yamamoto, T. et al., "A β-galactoside α2,6-sialyltransferase produced by a marine bacterium, Photobacterium leiognathi JT-SHIZ-145, is active at pH 8," Glycobiology, 2007, vol. 17(11), pp. 1167-1174.

Yamamoto, T. et al., "Cloning and Expression of a Marine Bacterial β-Galactoside α2,6-Sialyltransferase Gene from Photobacterium damsela JT0160," J. Biochem., 1998, vol. 123, pp. 94-100.

\* cited by examiner

PURIFICATION OF OLIGOSACCHARIDES

CROSS-REFERENCE TO RELATED APPLICATION

This application is a national stage entry pursuant to 35 U.S.C. § 371 of International Application No. PCT/IB2018/054750, filed on Jun. 27, 2018, which claims priority to each of DK Patent Application No. PA 2017 70522, filed on Jun. 30, 2017, DK Patent Application No. PA 2017 70523, filed on Jun. 30, 2017, and DK Patent Application No. PA 2017 70524, filed on Jun. 30, 2017, the contents of all of which are fully incorporated herein by reference.

FIELD OF THE INVENTION

This invention relates to a method for separating sialylated oligosaccharides, preferably sialylated human milk oligosaccharides (HMOs), from disaccharides, preferably lactose, produced by a fermentation or enzymatic process.

BACKGROUND OF THE INVENTION

In recent years, the manufacture and commercialization of complex carbohydrates including naturally secreted oligosaccharides have increased significantly due to their roles in numerous biological processes occurring in living organisms. Secreted oligosaccharides such as human milk oligosaccharides (HMOs) are carbohydrates which have gained much interest in recent years and are becoming important commercial targets for nutrition and therapeutic industries. In particular, the synthesis of these HMOs has increased significantly due to the role of HMOs in numerous biological processes occurring in humans. The great importance of HMOs is directly linked to their unique biological activities such as antibacterial, antiviral, immune system and cognitive development enhancing activities. Human milk oligosaccharides are found to act as prebiotics in the human intestinal system helping to develop and maintain the intestinal flora. Furthermore, they have also proved to be antiinflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Likewise, the compounds are also of interest in the medicinal industry for the production of therapeutics due to their prognostic use as immunomodulators. However, the syntheses and purification of these oligosaccharides and their intermediates remained a challenging task for science.

Sialylated human milk oligosaccharides such as disialyllacto-N-tetraose, 3'-O-sialyl-3-O-fucosyllactose, 6'-O-sialyllactose, 3'-O-sialyllactose, 6'-O-sialylated-lacto-N-neotetraose and 3'-O-sialylated-lacto-N-tetraose, are among the major components of human milk. In these sialylated human milk oligosaccharides the sialic acid residue is always linked to the 3-O— and/or 6-O— position of a terminal D-galactose or to the 6-O— position of a nonterminal GlcNAc residue via α-glycosidic linkages. Sialylated HMOs are thought to have significant health benefits for the neonate, because of their roles in supporting resistance to pathogens, gut maturation, immune function and cognitive development (ten Bruggencate et al. *Nutr. Rev.* 72, 377 (2014)).

Efforts to develop processes for synthesizing HMOs, including sialylated HMOs, have increased significantly in the last ten years due to their roles in numerous human biological processes. In this regard, processes have been developed for producing them by microbial fermentations, enzymatic processes, chemical syntheses, or combinations of these technologies. With regard to productivity, fermentation processes, on a lab scale, to produce 3'-SL and 6'-SL have proved to be promising.

However, to isolate sialylated lactoses or sialylated oligosaccharides from a complex matrix such as a fermentation broth is a challenging task. In these mixtures, the produced sialylated HMO is usually accompanied by contaminants and other impurities (of bacterial or chemical origin such as enzymes, proteins, protein fragments, endotoxins, DNA, carbohydrate by-products, salts, unreacted precursors, colour bodies, etc.) and the separation of the HMO product from those contaminants and impurities is necessary. A part of the problem is to separate the sialylated HMO product from lactose, since lactose is exogenously added, usually in excess, to the culture medium as a precursor to make the sialylated HMO. The same problem applies to enzymatic (ex vivo) production of sialylated HMOs from lactose.

Antoine et al. *Angew. Chem. Int. Ed.* 44, 1350 (2005) and US 2007/0020736 disclosed the production of 3'-SL and accompanying di- and trisialylated lactoses by a genetically modified *E. coli*; the broth containing approx. 0.8 mM 3'-SL was treated as follows: adsorption of the products from the centrifuged supernatant on charcoal/celite, washing away the water soluble salts with distilled water, eluting the compounds by gradient aqueous ethanol, separation of the sialylated products on a Biogel column and desalting, leading to 49 mg of 3'-SL from 1 litre of broth.

WO 01/04341 and Priem et al. *Glycobiology* 12, 235 (2002) disclosed the production of 3'-SL by a genetically modified *E. coli*; 3'-SL was isolated by the following sequence of operations: heat permeabilization of the producing cells followed by centrifugation, adsorption of the product from the supernatant on charcoal/celite, washing away the water soluble salts with distilled water, eluting the compound by gradient aqueous ethanol, binding the compound to a strong anion exchanger in $HCO_3^-$-form, elution of the compound with a linear gradient $NaHCO_3$— solution, then eliminating the sodium bicarbonate with a cation exchanger (in $H^+$-form), resulting in isolated 3'-SL with 49% purification yield.

WO 2007/101862 and Fierfort et al. *J. Biotechnol.* 134, 261 (2008) disclosed an alternative work-up procedure of a 3'-SL fermentation broth, the procedure comprising the steps of heat permeabilization of the producing cell, centrifugation, adjusting the pH of the extracellular to 3.0 by the addition of a strong cation exchanger resin in acid form, removal of the precipitated proteins by centrifugation, adjusting the pH of the supernatant to 6.0 by the addition of a weak anion exchanger in base form, binding the sialyllactose to an anion exchanger in $HCO_3^-$-form, after washing with distilled water, elution of the compound with a continuous gradient $NaHCO_3$— solution, eliminating the sodium bicarbonate with a cation exchanger (in $H^+$-form) until pH 3.0 was reached, then adjustment of the pH to 6.0 with NaOH. The above purification allowed to isolate 15 g of 3'-SL from 1 litre of broth containing 25.5 g of 3'-SL. Drouillard et al. *Carbohydr. Res.* 345, 1394 (2010)) applied Fierfort's procedure above to a fermentation broth containing 6'-SL (11 g/l) and some 6,6'-disialyllactose (DSL), and thus isolated 3.34 g 6'-SL+DSL in a ratio of 155/86.

WO 2006/034225 describes two alternative purifications of 3'-SL from a producing fermentation broth. According to the first procedure, the lysate from the culture was diluted with distilled water and stirred with activated charcoal/celite. The slurry was washed with water, then the product was eluted from the charcoal/celite with aq. ethanol. According to the second method, the culture cells were heat treated and the precipitated solids were separated from the supernatant by centrifugation. The resulting supernatant was processed through a microfilter, the permeate was passed through a 10 kDa membrane, then nanofiltered. The resulting retentate was then diafiltered to collect the final sample. Both purification methods provided 90-100 mg 3'-SL from 1 litre of fermentation broth.

Thus the isolation of sialylated oligosaccharides from fermentation broth is rather complex and cumbersome.

Aydoğan et al. (*Separ. Sci. Technol.* 33, 1767 (1998)) stated that nanofiltration is not a very suitable method for fractionation of sugars.

WO 98/15581 discloses the retention characteristics of salts and carbohydrates (lactose, sialyllactose, lacto-N-triose II, lacto-N-tetraose), and concludes that while both GE GH and GE GE polyamide membranes allow ions to pass, the GE GE membrane retains sialyllactose or similar trisaccharides more efficiently than the GE GH membrane. No conclusion about whether lactose could be separated from higher oligosaccharides was drawn.

Goulas et al. (*J. Sci. Food Agric.* 83, 675 (2003)) investigated the fractionating of commercial oligosaccharide mixtures by nanofiltration and observed that the rejection and permeate concentration values given by the membranes for the sugars during the filtration of single-sugar solutions would be not the same as if these sugars had been in a mixed solution.

WO 2005/067962 discloses the isolation of goat milk oligosaccharides comprising filtration of skimmed goat milk ultrafiltration permeate with a ceramic membrane of 1-5 kDa. Although a partial separation of salts and lactose is anticipated, the application is silent to quantify this. Nevertheless, the method further comprises active charcoal chromatography, ion exchange chromatography and electrodialysis to remove lactose and salts.

Luo et al. (*Biores. Technol.* 166, 9 (2014)) and Nordvang et al. (Separ. Purif. Technol. 138, 77 (2014)) tested the separation of enzymatically produced 3'-SL from lactose by nanofiltration; although a polyethersulphone (PES) membrane with a MWCO of 1000-1400 Da and a sulphonated PES membrane with a MWCO of 600-800 Da were suitable to separate the most of the lactose after diafiltration, the loss of 3'-SL was significant and its purity after separation was rather moderate, thus 3'-SL was further purified with anion exchange chromatography.

Accordingly, it is an object of the present invention to provide an improved method for separating a sialylated HMO from the reaction milieu in which it has been produced, especially from lactose that has been used as precursor in the fermentation or enzymatic production of said sialylated HMO, and which method provides sialylated HMOs in high purity without ion exchange chromatography.

SUMMARY OF THE INVENTION

In accordance with this invention, in a first aspect, a method is provided for separating a tri- or higher oligosaccharide containing a sialyl moiety from a feed solution comprising a disaccharide, particularly from an aqueous medium obtained from a fermentation or enzymatic process, comprising the steps in the following order:
a) contacting the feed solution with a polyamide nanofiltration membrane with a molecular weight cut-off (MWCO) of 600-3500 Da ensuring the retention of the tri- or higher oligosaccharide containing a sialyl moiety and allowing the disaccharide to pass, wherein the $MgSO_4$ rejection of the membrane is 50-90%,
b) conducting a diafiltration process on the retentate from step a), using said membrane, with an aqueous solution of an inorganic electrolyte, wherein the rejection of said electrolyte is not higher than that of $MgSO_4$, followed by optional diafiltration with pure water to remove excess of the electrolyte,
c) and collecting the retentate enriched in the tri- or higher oligosaccharide containing a sialyl moiety in the form of a salt with the cation of said electrolyte.

In a second aspect of the invention, a method is provided for separating a tri- or higher oligosaccharide containing a sialyl moiety from a feed solution comprising mono- and divalent salts, particularly from an aqueous medium obtained from a fermentation or enzymatic process, comprising the steps:
a) contacting the feed solution with a polyamide nanofiltration membrane with a molecular weight cut-off (MWCO) of 600-3500 Da ensuring the retention of the tri- or higher oligosaccharide containing a sialyl moiety and allowing the mono- and divalent salts to pass, wherein the $MgSO_4$ rejection of the membrane is 50-90%, by way of diafiltration with an aqueous solution of an inorganic electrolyte, wherein the rejection of said electrolyte is not higher than that of $MgSO_4$, followed by optional diafiltration with pure water to remove excess of the electrolyte,
b) and collecting the retentate enriched in the tri- or higher oligosaccharide containing a sialyl moiety in the form of a salt with the cation of said electrolyte.

In both aspects, preferably, the tri- or higher oligosaccharide containing a sialyl moiety comprises the disaccharide in its structure. The disaccharide, preferably, is a neutral (non-sialylated) disaccharide. More preferably, the tri- or higher oligosaccharide containing a sialyl moiety is a sialylated human milk oligosaccharide and the disaccharide is lactose.

Also preferably, the polyamide nanofiltration membrane is a thin-film composite (TFC) membrane.

Yet preferably, the polyamide nanofiltration membrane is a phenylene diamine or a piperazine membrane.

Also in accordance with this invention, in both aspects, before contacting the aqueous medium with the nanofiltration membrane, one or both of the following steps are carried out:
i) the aqueous medium is clarified to remove particulates and contaminants and advantageously also cell components and any insoluble metabolites and debris from a fermentation or enzymatic process; and/or
ii) substantially all proteins are removed from the aqueous medium, advantageously after the aqueous medium is clarified in step a).

DETAILED DESCRIPTION OF THE INVENTION

Terms and Definitions

The term "monosaccharide" means a sugar of 5-9 carbon atoms that is an aldose (e.g. D-glucose, D-galactose, D-mannose, D-ribose, D-arabinose, L-arabinose, D-xylose, etc.), a ketose (e.g. D-fructose, D-sorbose, D-tagatose, etc.), a deoxysugar (e.g. L-rhamnose, L-fucose, etc.), a deoxy-aminosugar (e.g. N-acetylglucosamine, N-acetylmannosamine, N-acetylgalactosamine, etc.), an uronic acid, a ketoaldonic acid (e.g. sialic acid) or equivalents.

The term "disaccharide" means a carbohydrate consisting of two monosaccharide units linked to each other by an interglycosidic linkage.

The term "tri- or higher oligosaccharide containing a sialyl moiety" means a sugar polymer consisting of at least three, preferably from three to eight, more preferably from three to six, monosaccharide units (vide supra), wherein at least one monosaccharide unit is sialic acid. The oligosaccharide can have a linear or branched structure containing monosaccharide units that are linked to each other by interglycosidic linkages.

The term "sialylated human milk oligosaccharide" or "sialylated HMO" means a complex carbohydrate found in human breast milk (Urashima et al.: *Milk Oligosaccharides*, Nova Medical Books, N.Y., 2011; Chen *Adv. Carbohydr. Chem. Biochem.* 72, 113 (2015)). The sialylated HMOs have a core structure being a lactose unit at the reducing end that may be elongated by one or more β-N-acetyl-lactosaminyl and/or one or more β-lacto-N-biosyl units, and which core structures are substituted by an α-N-acetyl-neuraminyl (sialyl) moiety. In this regard, the sialylated HMOs are charged or acidic molecules due to the presence of the sialyl moiety. Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

The term "sialyl" or "sialyl moiety" means the glycosyl residue of sialic acid (N-acetyl-neuraminic acid, Neu5Ac), preferably linked with α-linkage:

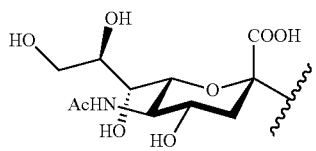

The term "fucosyl" means an L-fucopyranosyl group, preferably linked with α-interglycosidic linkage:

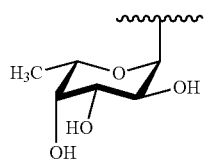

"N-acetyl-glucosaminyl" means an N-acetyl-2-amino-2-deoxy-D-glucopyranosyl (GlcNAc) group, preferably linked with β-linkage:

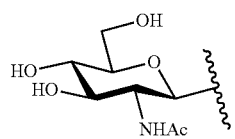

"N-acetyl-lactosaminyl" means the glycosyl residue of N-acetyl-lactosamine (LacNAc, Galpβ1-4GlcNAcp), preferably linked with β-linkage:

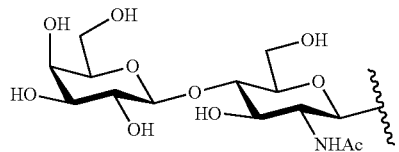

Furthermore, the term "lacto-N-biosyl" means the glycosyl residue of lacto-N-biose (LNB, Galpβ1-3GlcNAcp), preferably linked with β-linkage:

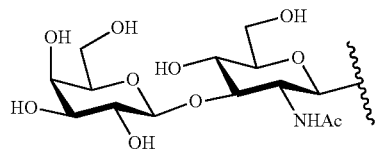

The term "aqueous medium [from a fermentation or enzymatic process]" preferably means an aqueous suspension resulting from an enzymatic or fermentation process for producing one or more hydrophilic oligosaccharides, preferably a sialylated HMO.

The term "protein-free aqueous medium" preferably means an aqueous medium or broth from a fermentation or enzymatic process, which has been treated to remove substantially all the proteins, as well as peptides, peptide fragments, RNA and DNA, as well as endotoxins and glycolipids that could interfere with the eventual purification of the one or more hydrophilic oligosaccharides, especially a sialylated HMO, from the fermentation or enzymatic process. Such removal of proteins, peptides, peptide fragments, RNA and DNA can be accomplished in a conventional manner by ion exchange chromatography, affinity chromatography, ultrafiltration, and size exclusion chromatography.

The term "clarified aqueous medium" preferably means an aqueous medium or broth from a fermentation or enzymatic process, which has been treated to remove suspended particulates and contaminants from the process, particularly cells, cell components, insoluble metabolites and debris from a fermentation process, that could interfere with the eventual purification of the one or more hydrophilic oligosaccharides, especially a sialylated HMO, from the fermentation or enzymatic process. Such a clarification treatment can be carried out in a conventional manner by centrifugation, flocculation, flocculation with optional ultrasonic treatment, gravity filtration, microfiltration, foam separation or vacuum filtration (e.g., through a ceramic filter which may include a Celite™ filter aid).

Rejection factor of a salt or an electrolyte (in percent) is calculated as $(1-\kappa_p/\kappa_r) \cdot 100$, wherein $\kappa_p$ is the conductivity of the salt in the permeate and $\kappa_r$ is the conductivity of the salt in the retentate. The retentate concentration is practically equal to the feed concentration concerning the salt. The procedure for measuring rejection of salts is disclosed in the examples.

Rejection factor of a carbohydrate (in percent) is calculated as $(1-C_p/C_r) \cdot 100$, wherein $C_p$ is the concentration of the carbohydrate in the permeate and $C_r$ is the concentration of the carbohydrate in the retentate. The retentate concentration is practically equal to the feed concentration concerning the carbohydrate. The procedure for measuring rejection of a carbohydrate is disclosed in the examples.

Separation factor concerning two carbohydrates is calculated as $(C_{p1}/C_{r1})/(C_{p2}/C_{r2})$, wherein $C_{p1}$ and $C_{p2}$ are the concentrations of the first and the second carbohydrate, respectively, in the permeate, and $C_{r1}$ and $C_{r2}$ are the concentrations of the first and the second carbohydrate, respectively, in the retentate.

"Pure water flux" is defined as the volume of purified water (e.g. distilled water, RO water) that passes through a membrane per unit time, per unit area and per unit of transmembrane pressure under specified conditions (at 23-25° C., 10 bar and constant cross-flow of 300 l/h). The procedure for measuring the pure water flux is disclosed in the working examples below.

Separating a Tri- or Higher Oligosaccharide Containing a Sialyl Moiety from a Disaccharide and/or Mono- and Divalent Salts The separation and therefore the purification of valuable oligosaccharides such as human milk oligosaccharides from the medium in which they have been produced, e.g. a fermentation broth or enzymatic reaction mixture, has always been a complicated multistep process due to the presence of numerous contaminants and by-products of different physical and chemical characters. One of the most difficult problem is to separate compounds of similar nature from each other, like to separate a desired carbohydrate from other, non-desired carbohydrates or separate charged compounds like tri- or higher oligosaccharide containing a sialyl moiety from ions (salts).

The present inventors have surprisingly found that a nanofiltration step significantly facilitates the separation and purification of charged oligosaccharides, advantageously sialylated human milk oligosaccharides, from a complex broth.

Accordingly, in a first aspect, a method is provided for separating a tri- or higher oligosaccharide containing a sialyl moiety from a disaccharide which are dissolved in a feed solution, particularly in an aqueous medium from a fermentation or enzymatic process, comprising the steps in the following order:
  a) contacting the feed solution with a nanofiltration membrane with a molecular weight cut-off (MWCO) of 600-3500 Da ensuring the retention of the tri- or higher oligosaccharide containing a sialyl moiety and allowing at least a part of the disaccharide to pass, wherein the active (top) layer of the membrane is composed of polyamide, and wherein the $MgSO_4$ rejection of the membrane is 50-90%,
  b) conducting a diafiltration process on the retentate from step a), using said membrane, with an aqueous solution of an inorganic electrolyte, wherein the rejection of said electrolyte is not higher than that of $MgSO_4$, followed by optional diafiltration with pure water to remove excess of the electrolyte,
  c) and collecting the retentate enriched in the tri- or higher oligosaccharide containing a sialyl moiety in the form of a salt with the cation of said electrolyte.

In a second aspect of the invention, a method is provided for separating a tri- or higher oligosaccharide containing a sialyl moiety from mono- and divalent salts which are dissolved in a feed solution, particularly in an aqueous medium from a fermentation or enzymatic process, comprising the steps:
  a) contacting the feed solution with a nanofiltration membrane with a molecular weight cut-off (MWCO) of 600-3500 Da ensuring the retention of the tri- or higher oligosaccharide containing a sialyl moiety and allowing at least a part of the mono- and divalent salts to pass, wherein the active (top) layer of the membrane is composed of polyamide, and wherein the $MgSO_4$ rejection of the membrane is 50-90%, by way of diafiltration with an aqueous solution of an inorganic electrolyte, wherein the rejection of said electrolyte is not higher than that of $MgSO_4$, followed by optional diafiltration with pure water to remove excess of the electrolyte,
  b) and collecting the retentate of step a) enriched in the tri- or higher oligosaccharide containing a sialyl moiety in the form of a salt with the cation of said electrolyte.

The term "ensuring the retention of the tri- or higher oligosaccharide containing a sialyl moiety" preferably means that, during the nanofiltration step, the tri- or higher oligosaccharides containing a sialyl moiety do not pass, or at least significantly do not pass, through the membrane and thus will be present in the retentate. The term "allowing at least a part of the disaccharide to pass through the membrane" preferably means, that the disaccharide, at least partially can penetrate the membrane and be collected in the permeate. In case of high rejection (about 90%) of the disaccharide, a subsequent diafiltration with pure water may be necessary to bring all or at least the majority of the disaccharide in the permeate. The higher the disaccharide rejection the more diafiltration water is necessary for efficient separation. The term "allowing at least a part of the mono- and divalent salts to pass through the membrane" preferably means, that the mono- and divalent salt, at least partially, but preferably their majority, can penetrate the membrane and be collected in the permeate. The mono- and divalent salts comprised in the feed solution are inorganic salts of mono- or divalent cations with mono- or divalent anions from strong inorganic acids and bases, and that are used e.g. as minerals in the fermentation process for producing tri- or higher oligosaccharide containing a sialyl moiety, or as a part of a buffer solution in an enzymatic reaction for producing tri- or higher oligosaccharide containing a sialyl moiety, or any salts formed in or after a fermentation or enzymatic process but prior to step a) in the method according to the second aspect of the invention, as a result of pH adjustment.

The applied nanofiltration membrane shall be tight for tri- and higher oligosaccharides in order that they are efficiently retained. Preferably, the rejection of the tri- or higher oligosaccharides containing a sialyl moiety is more than 95%, more preferably 97%, even more preferably 99%. Membranes with MWCO of more than 3500 Da are expected to allow more or significant amount of tri- or higher oligosaccharide pass through the membrane thus show a reduced retention of tri- or higher oligosaccharide containing a sialyl moiety and therefore are not suitable for the purposes of the invention, and can be excluded. In the same time, membranes with MWCO of less than 600 Da can also be excluded, because—together with the retention of tri- and higher oligosaccharides—that of the mono- and disaccharides is also expected, meaning that the overall separation of the compounds would likely be poor. In this regard, it is preferred that the rejection of the disaccharide is not more than 80-90%. If the disaccharide rejection turns to be 90±1-2%, the tri- or tetrasaccharide rejection shall preferably be around 99% or higher in order to achieve a practically satisfying separation.

It has been found that the above requirements are simultaneously fulfilled when the membrane is relatively loose for $MgSO_4$, that is its rejection is about 50-90%. In this regard the above specified membrane is tight for tri- and higher oligosaccharides, and loose for mono- and disaccharides, and as well as for $MgSO_4$. Therefore, it is possible to separate e.g. lactose, which is a precursor in making human milk oligosaccharides enzymatically or by fermentation, from the human milk oligosaccharides product by nanofiltration with a good efficacy, and additionally a substantial part of divalent ions also passes to the permeate. In some embodiments, the $MgSO_4$ rejection factor is 60-90%, 70-90%, 50-80%, 50-70%, 60-70% or 70-80%. Preferably, the $MgSO_4$ rejection factor on said membrane is 80-90%. Also preferably, the membrane has a rejection factor for NaCl that is lower than that for $MgSO_4$. In one embodiment, the rejection factor for NaCl is not more than 50%. In other embodiment, the rejection factor for NaCl is not more than 40%. In other embodiment, the rejection factor for NaCl is not more than 30%. In this latter embodiment a substantial reduction of all monovalent salts in the retentate is also achievable.

Also preferably, in some embodiments, the pure water flux of the membrane is at least 50 $l/m^2$ h. Preferably, the pure water flux of the membrane is at least 60 $l/m^2$ h, at least 70 $l/m^2$ h, at least 80 $l/m^2$ h or at least 90 $l/m^2$ h.

The active or the top layer of nanofiltration membrane suitable for the purpose of the invention is preferably made of polyamide. Although membranes of different type seem to have promising separation efficacy, for example NTR-7450 having sulphonated PES as active layer for separating lactose and 3'-SL (Luo et al. (Biores. Technol. 166, 9 (2014); Nordvang et al. (*Separ. Purif. Technol.* 138, 77 (2014)), the above specified membrane used in the invention shows always better separation of lactose from an HMO. In addition, the above mentioned NTR-7450 membrane is subject to fouling, which typically results in a drop in flux, increasing the lactose rejection and therefore a reduced separation factor (see examples). Also surprisingly, NTR-7450 membrane showed undesired lower retention of sialylated oligosaccharides at higher flux due to higher pressure applied.

Yet preferably, the polyamide membrane is a polyamide with phenylene diamine or piperazine building blocks as amine, more preferably piperazine (referred to as piperazine-based polyamide, too).

Yet preferably, the membrane suitable for the purpose of the present invention is a thin-film composite (TFC) membrane.

An example of suitable piperazine based polyamide TFC membranes is TriSep® UA60.

The claimed method applies a nanofiltration membrane characterized by some or all of the above features and thus one or more of the following benefits are provided: selectively and efficiently removes disaccharide, preferably lactose, from tri- or higher oligosaccharides containing a sialyl moiety, preferably sialylated HMOs, yielding an enriched tri- or higher oligosaccharide containing a sialyl moiety, preferably sialylated HMO, fraction; removes efficiently monovalent as well as divalent salts therefore no ion exchange step is necessary to obtain a tri- or higher oligosaccharide containing a sialyl moiety, preferably sialylated HMO, in high purity; higher flux during the nanofiltration/diafiltration can be maintained compared to other membranes used for the same or similar purpose in the prior art, which reduces the operation time; the membrane applied in the claimed method is less prone to getting clogged compared to the prior art solutions; the membrane applied in the claimed can be cleaned and regenerated completely therefore can be recycled without substantial reduction of its performance.

The nanofiltration membrane defined in the method of the invention is more beneficial compared to the prior art membranes used for the same or similar purpose as that of the present invention. Specifically, sulphonated PES membrane of Luo et al. or Nordvang et al. (NTR-7450, MWCO: 600-800, Nitto-Denko), besides showing lower separation factor of tri- to hexasaccharides over lactose, gets easily clogged; GE GE (polyamide, MWCO: 1000 Da) and GE GH (polyamide, MWCO: 2500 Da) membranes of WO 98/15581, besides showing lower separation factor of tri- to hexasaccharides over lactose, operate at lower flux and retain higher amount of salts in the permeate due to high NaCl rejection factor.

Accordingly, in one embodiment of the first aspect, a method is provided for separating a tri- or higher oligosaccharide from a disaccharide which are dissolved in a feed solution, particularly in an aqueous medium from a fermentation or enzymatic process, comprising:
  a) contacting the feed solution with a nanofiltration membrane with a molecular weight cut-off (MWCO) of 1000-3500 Da ensuring the retention of the tri- or higher oligosaccharide containing a sialyl moiety and allowing at least a part of the disaccharide to pass, wherein the active (top) layer of the membrane is composed of polyamide, and wherein the $MgSO_4$ rejection of the membrane is 80-90%, and wherein
  the NaCl rejection factor on said membrane is lower than that for $MgSO_4$, and/or
  the pure water flux value of said membrane is at least 50 $l/m^2$ h,
  b) conducting a diafiltration process on the retentate from step a), using said membrane, with an aqueous solution of an inorganic electrolyte, wherein the rejection of said electrolyte is not higher than that of $MgSO_4$, followed by optional diafiltration with pure water to remove excess of the electrolyte,
  c) and collecting the retentate enriched in the tri- or higher oligosaccharide containing a sialyl moiety in the form of a salt with the cation of said electrolyte.

In one embodiment of the second aspect, a method is provided for separating a tri- or higher oligosaccharide containing a sialyl moiety from mono- and divalent salts which are dissolved in a feed solution, particularly in an aqueous medium from a fermentation or enzymatic process, comprising the steps:
  a) contacting the feed solution with a nanofiltration membrane with a molecular weight cut-off (MWCO) of 1000-3500 Da ensuring the retention of the tri- or higher oligosaccharide containing a sialyl moiety and allowing at least a part of the mono- and divalent salts to pass, wherein the active (top) layer of the membrane is composed of polyamide, and wherein the $MgSO_4$ rejection of the membrane is 80-90%, by way of diafiltration with an aqueous solution of an inorganic electrolyte, wherein the rejection of said electrolyte is not higher than that of $MgSO_4$, followed by optional diafiltration with pure water to remove excess of the electrolyte,
  b) and collecting the retentate of step a) enriched in the tri- or higher oligosaccharide containing a sialyl moiety in the form of a salt with the cation of said electrolyte.

Preferably, in both embodiments disclosed above, the NaCl rejection factor of the membrane is at most the half of the $MgSO_4$ rejection factor.

More preferably, the nanofiltration membrane to be applied in the claimed invention:

is a piperazine-based polyamide membrane with a MWCO of 1000-3500 Da, has a $MgSO_4$ rejection of 50-90%, preferably 80-90%, has a NaCl rejection of not more than 30%, and has a pure water flux value of at least 50 l/m² h, preferably 90 l/m² h.

Also in a preferred embodiment, the structure of the tri- or higher oligosaccharide containing a sialyl moiety comprises the structure of the disaccharide, which disaccharide is to be separated from the tri- or higher oligosaccharide containing a sialyl moiety by the method of invention. Accordingly, the tri- or higher oligosaccharides containing a sialyl moiety are derivatives of the disaccharide, namely they are glycosylated variants of the particular disaccharide, wherein at least one glycosyl moiety is sialyl. If the disaccharide is glycosylated by adding one monosaccharide unit, it results in a trisaccharide comprising the disaccharide moiety; if the disaccharide is glycosylated by adding two monosaccharide units, it results in a tetrasaccharide comprising the disaccharide moiety; etc. The matching combinations of the disaccharide and the tri- or higher oligosaccharide containing a sialyl moiety are due to the practical reason that the tri- or higher oligosaccharides containing a sialyl moiety are produced from the disaccharide as a precursor by chemical, enzymatic or fermentative ways, especially enzymatically or by fermentation, and the disaccharide left in the reaction mixture as unreacted or because it was added in excess.

According to a more preferred embodiment, the disaccharide is lactose and the tri- or higher oligosaccharide containing a sialyl moiety is a glycosylated lactose, wherein at least one glycosyl moiety is sialyl. In this regard, concerning the above more preferred embodiment, the trisaccharide containing a sialyl moiety is a sialylated lactose; a tetrasaccharide containing a sialyl moiety is a double glycosylated lactose wherein at least one of the two glycosyl groups is sialyl, which sialyl group may be directly attached to the lactose or the other glycosyl group provided that the other glycosyl group is not sialyl, and preferably the other glycosyl group is a fucosyl or N-acetylglucosaminyl; a pentasaccharide containing a sialyl moiety is a triple glycosylated lactose wherein at least one of the three glycosyl groups is sialyl, which sialyl group may be directly attached to the lactose or one of the other two glycosyl groups provided that that other glycosyl group is not sialyl, and preferably the other two glycosyl groups consists of a N-acetylglucosaminyl and a galactosyl moiety attached to each other to form a lacto-N-biosyl or a N-acetyllactosaminyl moiety. Particularly, tri- or higher oligosaccharide containing a sialyl moiety is a sialylated (charged) HMO, preferably selected from the list consisting of 3'-SL, 6'-SL, FSL, LST a, LST b, LST c, FLST a, FLST b, FLST c and DS-LNT. Particularly preferred sialylated HMOs are 3'-SL and 6'-SL.

Also in a preferred embodiment, the separation factor of a disaccharide over a tri- or higher oligosaccharide containing a sialyl moiety is more than 5, preferably more than 10, more preferably more than 25, even more preferably more than 100. Especially, the separation factor of lactose over a sialylated human milk oligosaccharide is more than 10, preferably more than 25, more preferably more than 50, even more preferably more than 100.

Yet preferably, the separation factor of a disaccharide over a trisaccharide containing a sialyl moiety is more than 5, preferably more than 10, more preferably more than 25. Especially, the separation factor of lactose over 3'-SL or 6'-SL is more than 20, preferably more than 50.

Yet preferably, the separation factor of a disaccharide over a tetra- or pentasaccharide containing a sialyl moiety is more than 25, preferably more than 50, more preferably more than 100.

The method of the invention can be conducted under conditions used for conventional nanofiltration or nanofiltration/diafiltration with tangential flow or cross-flow filtration with positive pressure compared to permeate side where both operations could be performed in a batch mode or preferably in continuous mode. The diafiltration is conducted, in the first aspect of the invention, by adding pure water or an electrolyte to the retentate after the nanofiltration according to step a) disclosed above and continuing the filtration process. The diafiltration is conducted, in the second aspect of the invention, by adding pure water or an electrolyte directly to the feed solution.

In both aspects, the diafiltration is performed with an aqueous solution of an inorganic electrolyte. The inorganic electrolyte implies an inorganic salt that is at least partially soluble, preferably well soluble in water. The rejection of the inorganic salt on the membrane used in the method of invention shall not be higher than that of $MgSO_4$. In one embodiment, the aqueous solution of the inorganic electrolyte (salt) is neutral, that is a salt of a strong inorganic acid and a strong inorganic base. Exemplary embodiments of strong inorganic acids are HCl, HBr, sulfuric acid, nitric acid, phosphoric acid and perchloric acid, and those of strong inorganic bases are NaOH, KOH, LiOH, $Mg(OH)_2$ and $Ca(OH)_2$; the salts formed from these acid and bases are comprised in the group of neutral inorganic electrolytes applicable for the purpose of the invention. In other embodiment, the aqueous solution of the inorganic electrolyte is slightly basic, this is the case when a strong inorganic base (see above) forms a salt with a weak inorganic acid, e.g. carbonic acid (making carbonates) or acetic acid (making acetates).

The inorganic electrolyte, usually, is an univalent or a bivalent anion electrolyte. Univalent anion electrolytes are e.g. the salts of HCl, HBr, nitric acid or perchloric acid, particularly chlorides such as LiCl, NaCl, KCl, $MgCl_2$, $CaCl_2$, or bicarbonates such as $NaHCO_3$. Divalent anion electrolytes are e.g. the salts of sulfuric acid such as $Na_2SO_4$, $K_2SO_4$, $MgSO_4$, $Na_2SO_4$, or carbonates such as $Na_2CO_3$, $K_2CO_3$. Especially preferred inorganic electrolyte is NaCl.

Preferably, the aqueous solution of an inorganic electrolyte used in the diafiltration is a single electrolyte, that is the aqueous solution contains one and only electrolyte (salt).

The diafiltration membrane shall ensure the high retention of the tri- or higher oligosaccharide containing a sialyl moiety and allow the electrolyte to pass. In this regard the membrane used in the diafiltration step is preferably the one defined in both methods of the invention.

Diafiltration step b) can be conducted with feeding an electrolyte or pure water to the retentate or the feed, as the case may be, with constant removal of permeate. The preferred mode of an electrolyte or water addition is continuous, i.e. the addition flow rate is matching approximately the permeate flow rate. The addition of electrolyte is terminated when the desired degree of replacement, e.g. 99% or more, of unwanted salts is achieved. Then the excess of electrolyte can be removed completely or to the acceptable low level by diafiltration with pure water, which could be monitored for example by substantial reduction in conductivity of a permeate stream to a constant low level.

During diafiltration step, a tri- or higher oligosaccharide containing a sialyl moiety, preferably a sialylated HMO, particularly 3'-SL or 6'-SL, obtained in the retentate after step a) (in the first aspect), or containing in the feed (in the second aspect), is subjected to salt exchange with the inorganic electrolyte. The tri- or higher oligosaccharide containing a sialyl moiety as dissolved in the retentate or the feed may be in non-uniform form, meaning that—depending on how and under which conditions it has been previously synthesized—it may occur in partially acid and salt form, moreover the cations of the salt can be mixed, e.g. those employed in the fermentation medium as nutrients for the producing cell or in the enzymatic reaction as buffer. The diafiltration is conducted for sufficient time that the cations of the tri- or higher oligosaccharide containing a sialyl moiety are exchanged to the cation of the electrolyte employed; e.g. if the tri- or higher oligosaccharide containing a sialyl moiety is 3'-SL and the electrolyte is NaCl, substantially all amount of 3'-SL is converted to 3'-SL sodium salt. In this regard, the tri- or higher oligosaccharide containing a sialyl moiety is brought to a single and uniform salt form at the end of the diafiltration step.

Optionally, the diafiltration may comprise addition of pure water after diafiltration with the aqueous solution with an inorganic electrolyte. This optional step is advisable when the rejection of the inorganic electrolyte on the membrane specified in the method is close to that of $MgSO_4$.

By the pure water diafiltration substantially all uni- and divalent salts can be removed to the filtrate.

Both methods comprising diafiltration described above provides a retentate solution that contains a particular salt of the tri- or higher oligosaccharide containing a sialyl moiety and practically lacks any uni- and divalent salts. Therefore, a salt of a tri- or higher oligosaccharide containing a sialyl moiety is available in uniform salt form and high purity or essay in a simple way, and no further purification steps such ion exchange treatment, as suggested by the prior art, is necessary.

The pH of the feed solution applied for the NF separation or the NF/DF step according to the present invention is not higher than 7, preferably between 3 and 7, more preferably around 4 and 5. Too low pH may influence the membrane's and the solute's properties adversely.

The convenient temperature range applied is between 10 and 80° C. Higher temperature provides a higher flux and thus accelerates the process. The membrane is expected to be more open for flow-through at higher temperatures, however this doesn't change the separation factors significantly. A preferred temperature range for conducting the nanofiltration separation according to the invention is 20-45° C.

The applied pressure in the nanofiltration and nanofiltration/diafiltration separation is about 2-50 bars, the higher the pressure the higher the flux.

In step c) of the method according to the first aspect or in step b) according to the second aspect of the invention, the salt of a tri- or higher oligosaccharide containing a sialyl moiety can then be isolated from the aqueous solution obtained as retentate after diafiltration in solid form in a conventional manner, e.g. by evaporation, spray-drying drying (see e.g. WO 2013/185780), crystallization (see e.g. WO 2010/116317, WO 2017/086443) or lyophilization.

The sialylated HMOs can be produced from lactose in a conventional manner enzymatically and/or by fermentation of genetically transformed bacteria in an aqueous medium or broth. In this regard, for fermentation methods see for example WO 01/04341, WO 2006/034225, US 2007/0020736, WO 2007/101862, WO 2014/153253, Priem at al. *Glycobiology* 12, 235 (2002), Antoine et al. *Angew. Chem. Int. Ed.* 44, 1350 (2005), Fierfort et al. *J. Biotechnol.* 134, 261 (2008), Drouillard et al. *Carbohydr. Res.* 345, 1394 (2010). For enzymatic syntheses, see for example WO 96/32492, WO 99/31224, Maru et al. *Biosci. Biotech. Biochem.* 56, 1557 (1992), Gilbert et al. *Nature Biotechnol.* 16, 769 (1998), Masuda et al. *J. Biosci. Bioeng.* 89, 119 (2000), Mine et al. *J. Carbohydr. Chem.* 29, 51 (2010), Luo et al. *Biores. Technol.* 166, 9 (2014), Nordvang et al. *Separ. Purif. Technol.* 138, 77 (2014).

In carrying out this invention, an aqueous medium, which can come directly from an enzymatic or preferably a fermentation process, particularly from *E. coli* or yeast fermentation, and which contains the tri- or higher oligosaccharide containing a sialyl moiety accompanied by different contaminants, is optionally treated by, preferably prior step a) according to both aspects, the following steps:
  i) clarifying the aqueous medium to remove suspended particulates and contaminants, particularly cells, cell components, insoluble metabolites and debris from a fermentation process; and/or
  ii) removing substantially all the proteins, as well as peptides, RNA and DNA and any endotoxins and glycolipids that could interfere with the subsequent purification step, from the aqueous medium, preferably after clarifying it.

In step i), the aqueous medium, which contains the tri- or higher oligosaccharide containing a sialyl moiety, is clarified in a conventional manner, e.g. by centrifugation or ultrafiltration. Preferably the aqueous medium is first flocculated and then centrifuged or filtered to remove any remaining insoluble particulates and contaminants, as well as cells and cell components and insoluble metabolites and debris.

In step ii), proteins and related impurities are removed from the aqueous medium in a conventional manner, e.g. by a second ultrafiltration step or tangential flow ultrafiltration.

According to steps i) or ii), the broth obtained from fermentation is subjected to ultrafiltration. The fermentation broth typically contains, besides the N-acetylglucosamine containing neutral oligosaccharides produced, the biomass of the cells of the used microorganism together with proteins, protein fragments, DNA, endotoxins, biogenic amines, inorganic salts, unreacted carbohydrate acceptor such as lactose, sugar-like by-products, monosaccharides, colorizing bodies, etc. The ultrafiltration step is to separate the biomass and, preferably, also high molecular weight suspended solids from the soluble components of the broth which pass through the ultrafiltration membrane in the permeate. This UF permeate (UFP) is an aqueous solution containing the produced tri- or higher oligosaccharide containing a sialyl moiety.

Any conventional ultrafiltration membrane can be used having a molecular weight cut-off (MWCO) range between about 1 and about 500 kDa, such as 10-250, 50-100, 200-500, 100-250, 5-100, 5-50, 10-25, or any other suitable sub-ranges. The membrane material can be a ceramic or made of a synthetic or natural polymer, e.g. polysulfone, polypropylene, cellulose acetate or polylactic acid. The ultrafiltration step can be applied in dead-end or cross-flow mode. These steps may comprise more than one ultrafiltration step using membranes with different MWCO, e.g. using two ultrafiltration separations wherein the first membrane has a higher MWCO than that of the second membrane. This arrangement may provide a better separation efficacy of the higher molecular weight components of the broth. After this separation step the permeate contains materials that have a molecular weight lower than the MWCO of the second membrane, including the oligosaccharide of interest.

The one or more sialylated HMOs separated from lactose and/or mono- and divalent salts and therefore purified by the method of invention can then be isolated from the aqueous retentate and from the optional the aqueous wash in a conventional manner, e.g. by evaporation, freeze drying, crystallization or lyophilisation.

EXAMPLES

Example 1

Determination of a Substance Rejection Factor on a Membrane

The NaCl and MgSO$_4$ rejection on a membrane is determined as follows: in a membrane filtration system, a NaCl (0.1%) or a MgSO$_4$ (0.2%) solution is circulated across the selected membrane sheet with (for Tami: tubular module) while the permeate stream is circulated back into the feed tank. The system is equilibrated at 10 bars and 25° C. for 10 minutes before taking samples from the permeate and retentate. The rejection factor is calculated from the measured conductivity of the samples: $(1-\kappa_p/\kappa_r)\cdot 100$, wherein $\kappa_p$ is the conductivity of NaCl or MgSO$_4$ in the permeate and $\kappa_r$ is the conductivity of NaCl or MgSO$_4$ in the retentate.

|  |  |  | NaCl rej. factor | | MgSO$_4$ rej. factor | |
| --- | --- | --- | --- | --- | --- | --- |
| membrane | active layer | MWCO | supplier spec. | lab. measurement | supplier spec. | lab. measurement |
| Trisep UA60 | piperazine-PA | 1000-3500 | — | 10% | 80% | 81-89% |
| GE GH | PA | 2500 | — | 81% | — | 76% |
| NTR-7450 | sulph. PES | 600-800 | 50% | 56% | — | 32% |
| Tami | ceramic | 1000 | — | — | — | 0% |

A carbohydrate rejection factor is determined in a similar way with the difference that the rejection factor is calculated from the concentration of the samples (determined by HPLC): $(1-C_p/C_r)\cdot 100$, wherein $C_p$ is the concentration of the carbohydrate in the permeate and $C_r$ is the concentration of the carbohydrate in the retentate.

Example 2

3'-SL was made by fermentation using a genetically modified *E. coli* cell of LacZ$^-$, LacY$^+$ phenotype carrying heterologous neuBCA, wherein said cell comprises a recombinant gene encoding an α-2,3-sialyl transferase which is able to transfer the sialic acid of GMP-sialic acid to the internalized lactose, and deleted or inactivated nanKETA. The fermentation was performed by culturing said cell in the presence of exogenously added lactose and a suitable carbon source, thereby producing 3'-SL. The obtained fermentation broth containing 3'-SL was divided into two parts and they were subjected to cell removal by centrifugation with additional washing of separated cell debris. The obtained clarified supernatants (feed #1: 5.2 kg; feed #2: 4.5 kg) were combined and passed through a UF membrane (Synder XT2B-1812F, 1 kDa) installed into MMS SW18 membrane filtration system at p=8 bar, T=40° C. and a cross-flow of approximately 300 l/h. After most of the solution was passed through, the remaining retentate (ca. 2 l) was diafiltrated with 5 l of water to give 13 kg of combined permeate. It was concentrated by nanofiltration using a tight membrane (Synder NFG-2B-1812F, MWCO 600-800 Da) with subsequent diafiltration applying 10 l of water to give cca. 2000 g of retentate (NF1 retentate). A sample from NF1 was taken and freeze-dried (100 ml=103.5 g gave 10.5 g of a solid) and analysed for ion composition and carbohydrate content. NF1 was de-colorized with 25 g of activated charcoal then concentrated under reduced pressure and freeze-dried to give 173.7 g of white solid of crude 3'-SL—mixed salt containing K$^+$, Mg$^{2+}$ and Na$^+$ as major counter-ions.

Part of the obtained freeze-dried solid (90 g) was re-dissolved in water (1.5 l) and diafiltrated continuously through Trisep TurboClean 1812-UA60-31 membrane (piperazine PA, MWCO1000-3500 Da, measured MgSO$_4$ rejection is 89%) using 10 l of 1% NaCl solution at a cross-flow of 300 l/h, p=20 bar, T=20-25° C. and initial pH=5.2. Then excess of NaCl was removed by additional diafiltration with 10 l of deionized water until constant and low conductivity of the permeate (0.068 mS/cm vs 5.89 mS/cm before diafiltration). The so-obtained retentate was pumped out from the system to give 794 g of 3'-SL solution (an estimated dead volume of 119 g remained in the system). A sample from this retentate (300 g) was freeze-dried to give 3'-SL Na salt as a white solid (27 g, NF2-retentate). The remaining solution plus washes from the system gave additional 42 g of the final product after freeze-drying. Estimated yield of the diafiltration step is 88%. The analytical data are summarized in the table below.

|  | feed#1 (after cell removal) | feed#2 (after cell removal) | NF1 retentate | NF1 retentate after activated charcoal | NF2 retentate after DF with NaCl |
| --- | --- | --- | --- | --- | --- |
| 3'-SL assay NMR (acid form) |  |  |  |  | 88.5% |
| 3'-SL assay HPAEC | 69.74% | 49.82% | 88.54% | 89.53% | 84.1% |
| Na (theoretical: 3.27 %) | 0.53% | 0.45% | 0.55% | 0.57% | 3.06% |
| H$_2$O (KF) |  |  |  |  | 6.97 |
| Impurities | | | | | |
| lactose | n.a. | 0.43% | 0 | 0 | 0 |
| sialic acid | 6.0% | 6.42% | 0.17% | 0.23% | 0 |
| potassium | 1.53% | 5.04% | 2.44% | 2.51% | 0.0060% |

-continued

|  | feed#1 (after cell removal) | feed#2 (after cell removal) | NF1 retentate | NF1 retentate after activated charcoal | NF2 retentate after DF with NaCl |
|---|---|---|---|---|---|
| magnesium | 0.22% | 0.31% | 0.55% | 0.53% | 0.0150% |
| calcium | 0.005% | 0.0046% | 0.0046% | 0.0083% | <0.0010% |
| ammonia | n.a. | n.a. | n.a. | 1.71% | n.d. (0) |
| orthophosphate | 0.52% | 7.06% | 0.46% | 0.46% | n.d. (0) |
| sulphate | 0.42% | 0.16% | 0.0015% | 0.0012% | <0.05% |
| proteins (Bradford assay) | 1.52% | 2.98% | 879 ppm | 82 ppm | 0.0074% |

Example 3

6'-SL was made by fermentation using a genetically modified E. coli cell of LacZ$^-$, LacY$^+$ phenotype carrying heterologous neuBCA, wherein said cell comprises a recombinant gene encoding an α-2,6-sialyl transferase which is able to transfer the sialic acid of GMP-sialic acid to the internalized lactose, and deleted or inactivated nanKETA. The fermentation was performed by culturing said cell in the presence of exogenously added lactose and a suitable carbon source, thereby producing 6'-SL. The obtained fermentation broth containing 6'-SL (ca. 600 l) was subjected to cell removal by ultrafiltration/diafiltration (ceramic membrane, MWCO 15 kDa), followed by charcoal treatment and partial concentration by nanofiltration (MWCO 150-300 Da). Part of the obtained solution (36.4 kg) was divided into 8 portions (cca. 4.5 kg each, 6'-SL content: 25.4 g/l, total 6'-SL content: 924 g). Each portion was acidified with acetic acid to adjust the pH to 5.0 and subjected to further enrichment by additional cross-flow ultrafiltration (UF) in a first membrane filtration equipment (1 kDa, Synder XT-1812-2B spiral-wound membrane, pressure: 20-30 bar, T=20-30° C.; 6'-SL rejection 31%) and the permeate stream (that contains 6'-SL) was immediately processed by nanofiltration (NF) (Trisep 1812-UA60-31, piperazine PA, MWCO1000-3500 Da, measured MgSO$_4$ rejection is 89%; 6'-SL rejection 99.8%, separation factor over lactose: 170) in a second membrane filtration equipment. When most of the feed was passed through the UF membrane, the remaining part was diafiltered and the permeate was processed by the second (NF) membrane filtration equipment. At the end of UF/DF in the first equipment, the UF retentate contained 0.8% of the original amount of 6'-SL in the feed, showing that practically all 6'-SL passed through the UF membrane to the feed of the NF and processed by NF. Them, diafiltration (DF) was conducted in the second (NF) unit at p=30-35 bar and T=30-35° C. with 20 l of 2% NaCl solution followed by 20 l of deionized water at approximately 8.9 l/h feed rate matching the permeate flow rate. After completion of the addition of the DF water, the retentate was further concentrated at p=40 bar until permeate flux dropped to 14 l/m$^2$ h. In the end of the NF/DF process in the second equipment, the retentates of all 8 batches were combined to give 4.3 kg of 6'-SL Na-salt solution (6'-SL amount is 886 g, 92%). A small sample was freeze-dried (50 ml=54.2 g gave 10.9 g of a solid) and analysed. The obtained remaining retentate was treated with activated charcoal, filtered and freeze-dried to give 845 g of the final 6'-SL Na-salt as a white solid (assay by HPAEC: 95.25%, Na$^+$: 3.1% [theoretical: 3.27%], K$^+$: 0.026%, Mg$^{2+}$: 0.009%, PO$_4^{3-}$: 0.0137%, SO$_4^{2-}$: 0.076%).

Example 4

The nanofiltration membranes are, in general, subject to fouling due to the presence of larger molecules in the feed solution like peptide fragments, lipids, anti-foam, etc., which causes a drop in flux and/or decrease the separation factor. The purpose of this investigation is how the membranes can be cleaned and regenerated.

Flat sheet membranes (d=20 cm, active membrane area 280 cm$^2$ for each sheet) were installed into a cross-flow flat sheet cell of the MMS SW18 membrane filtration system. Pure water was equilibrated at 10 bars and 23-25° C. with constant cross-flow (300 l/h) for at least 10 min. Then small portion (5-30 ml) of permeate fractions were collected and exact mass or volume was measured. Flux was calculated according to the following formula: $F=V/(t \cdot A)$ where V is the collected permeate volume in litres, t is the time required to collect the measured volume in hours and A is the membrane area in m$^2$.

The following pure water flux values were measured:

| membrane | active layer | MWCO | flux (l/m$^2$h) |
|---|---|---|---|
| Trisep UA60 | piperazine-PA | 1000-3500 | 100.8 |
| GE GH | PA | 2500 | 17 |
| NTR-7450 | sulph. PES | 600-800 | 99.6 |

Then, for the Trisep UA60 and Nitto-Denko NTR-7450 membranes, water was replaced by a feed solution which was prepared as follows: crude LNnT solid sample was obtained from fermentation broth after cell removal by UF (15 kDa), NF (150-300 Da) with diafiltration, decolouration with activated charcoal and freeze-drying. The obtained solid contained LNnT (54.6%), lactose (9.86%), lacto-N-triose II (7.32%) and pLNnH (8.67%, all by weight), from which 41 g was dissolved in 2050 g of water, obtaining a solution having a pH of 5.71 and conductivity of 0.825 mS/cm. The flux of the feed solution was measured under the same conditions.

Then the membranes were washed with pure water (cleaning in place, CIP1), and water flux was re-measured.

Following this, the membranes were washed with an aqueous cleaning solution containing 0.1% sodium dodecyl sulphate, 0.5% EDTA and 0.5% sodium tripolyphosphate (cleaning in place, CIP2, 30 min, 5 bar, 20-25° C.), and water flux was remeasured.

The data show that the NTR-7450 membrane is more prone to being fouled than Trisep UA60 when a pre-treated oligosaccharide solution obtained after fermentation is applied. Furthermore, while pure water washing regenerated the Trisep UA60 membrane to reach 85% of the original water flux, it was inefficient to do so for the NTR-7450 membrane. In addition, whereas a detergent containing cleaning solution completely cleaned the Trisep UA60 membrane, the NTR-4750 membrane was regenerated only partially.

|  | flux (l/m2h) | |
| --- | --- | --- |
|  | Trisep UA60 | NTR-7450 |
| initial water flux | 100.8 | 99.6 |
| flux with feed solution | 55.1 | 30.3 |
| water flux after CIP1 | 85.4 | 23.9 |
| after CIP1 relative to initial | 85% | 24% |
| water flux after CIP2 | 119 | 71.3 |
| after CIP2 relative to initial | 118% | 72% |

The invention claimed is:

1. A method for separating a tri- or higher oligosaccharide containing a sialyl moiety from a disaccharide in an aqueous medium from fermentation or enzymatic reaction, comprising the steps in the following order:
   a) contacting the aqueous medium with a nanofiltration membrane with a molecular weight cut-off (MWCO) of 600-3500 Da ensuring the retention of the tri- or higher oligosaccharide containing a sialyl moiety and allowing at least a part of the disaccharide to pass, wherein the membrane comprises an active layer of polyamide, a $MgSO_4$ rejection of 50-90%, and a NaCl rejection lower than the $MgSO_4$ rejection,
   b) conducting a diafiltration process on a retentate from step a), using said membrane, with an aqueous solution of an inorganic electrolyte, wherein the membrane comprises a rejection of said electrolyte not higher than that of $MgSO_4$, and
   c) collecting a second retentate enriched from step b) in the tri- or higher oligosaccharide containing a sialyl moiety in the form of a salt from the cation of said electrolyte.

2. The method according to claim 1, and the NaCl rejection of the membrane is not more than 30%.

3. The method according to claim 1, wherein the aqueous solution of an inorganic electrolyte is a neutral solute comprising a single electrolyte, and the single electrolyte is sodium chloride.

4. The method according to claim 1, wherein the polyamide nanofiltration membrane is a piperazine-based membrane.

5. The method according to claim 1, wherein the tri- or higher oligosaccharide containing a sialyl moiety comprises said disaccharide in its structure.

6. The method according to claim 5, wherein said disaccharide is lactose.

7. The method according to claim 6, wherein the tri- or higher oligosaccharide containing a sialyl moiety is a sialylated human milk oligosaccharide (HMO).

8. The method according to claim 7, wherein the HMO is produced by fermentation or enzymatically from lactose as precursor.

9. The method according to claim 8, wherein step a) is preceded by at least one of the following steps:
   i) clarifying the aqueous medium from fermentation or enzymatic reaction to remove suspended particulates and contaminants; and/or
   ii) removing protein from the aqueous medium of the fermentation or enzymatic reaction.

10. The method according to claim 9, wherein at least one of the steps i) and ii) comprises ultrafiltration.

11. The method according to claim 9, wherein step ii) further comprises removing peptides, RNA, DNA, endotoxins and glycolipids from the aqueous medium.

12. A method for separating a tri- or higher oligosaccharide containing a sialyl moiety from mono- and divalent salts which are dissolved in an aqueous medium from fermentation or enzymatic reaction, comprising the steps:
   a) contacting the aqueous medium with a nanofiltration membrane with a molecular weight cut-off (MWCO) of 600-3500 Da ensuring the retention of the tri- or higher oligosaccharide containing a sialyl moiety and allowing at least a part of the mono- and divalent salts to pass, wherein the membrane comprises an active layer of polyamide, and a MgSO4 rejection of 50-90%, and conducting diafiltration of the aqueous solution with an aqueous medium of an inorganic electrolyte, wherein the membrane comprises a rejection of said electrolyte not higher than that of MgSO4, and
   b) collecting a retentate of step a) enriched in the tri- or higher oligosaccharide containing a sialyl moiety in the form of a salt with the cation of said electrolyte.

13. The method according to claim 12, wherein the aqueous solution of an inorganic electrolyte is a neutral solute.

14. The method according to claim 13, wherein the neutral solute is a single electrolyte, and the single electrolyte is a uni- or divalent single electrolyte.

15. The method according to claim 14, wherein the univalent single electrolyte is sodium chloride.

16. The method according to claim 15, wherein the membrane comprises a NaCl rejection lower than the $MgSO_4$ rejection, and the NaCl rejection of the membrane is not more than 30%.

17. The method according to claim 12, wherein the polyamide nanofiltration membrane is a piperazine-based membrane.

18. The method according to claim 12, wherein the tri- or higher oligosaccharide containing a sialyl moiety is a sialylated human milk oligosaccharide (HMO).

19. The method according to claim 18, wherein the HMO is produced by fermentation or enzymatically from lactose as precursor.

20. The method according to claim 19, wherein step a) is preceded by at least one of the following steps:
   i) clarifying the aqueous medium from fermentation or enzymatic reaction to remove suspended particulates and contaminants; and/or
   ii) removing protein from the aqueous medium of the fermentation or enzymatic reaction.

* * * * *